United States Patent
Ito et al.

(10) Patent No.: US 6,727,336 B1
(45) Date of Patent: Apr. 27, 2004

(54) OCULAR LENS MATERIALS AND PROCESS FOR PRODUCING THE SAME

(75) Inventors: Eri Ito, Kasugai (JP); Tetsuji Kawai, Kasugai (JP); Sadanori Oono, Kasugai (JP); Kazuhiko Nakada, Kasugai (JP); Misako Nishibayashi, Kasugai (JP)

(73) Assignee: Menicon Co., Ltd., Nagoya (JP)

( * ) Notice: Subject to any disclaimer, the term of this patent is extended or adjusted under 35 U.S.C. 154(b) by 0 days.

(21) Appl. No.: 09/926,459

(22) PCT Filed: May 9, 2000

(86) PCT No.: PCT/JP00/02939
§ 371 (c)(1),
(2), (4) Date: Nov. 7, 2001

(87) PCT Pub. No.: WO00/70388
PCT Pub. Date: Nov. 23, 2000

(30) Foreign Application Priority Data

May 12, 1999 (JP) .......................................... 11-131678

(51) Int. Cl.$^7$ ............................................. C08F 230/08
(52) U.S. Cl. ................ 526/279; 351/160 H; 351/160 R
(58) Field of Search ..................... 526/279; 351/160 H, 351/160 R

(56) References Cited

U.S. PATENT DOCUMENTS

| | | | | |
|---|---|---|---|---|
| 4,136,250 A | * | 1/1979 | Mueller et al. ................ | 528/29 |
| 4,410,674 A | | 10/1983 | Ivani ........................... | 526/279 |
| 4,500,695 A | | 2/1985 | Ivani ........................... | 526/279 |
| 5,244,470 A | | 9/1993 | Onda et al. .................... | 8/507 |
| 5,413,863 A | * | 5/1995 | Weber et al. ................ | 428/428 |
| 6,440,571 B1 | * | 8/2002 | Valint, Jr. et al. ........... | 428/447 |

FOREIGN PATENT DOCUMENTS

| EP | 584 764 A1 | 3/1994 |
|---|---|---|
| EP | 637 761 A1 | 2/1995 |
| JP | 63 163811 | 7/1988 |
| JP | 6-102472 | 4/1994 |
| JP | 8-245652 | 9/1996 |
| JP | 11-287971 | 10/1999 |

* cited by examiner

*Primary Examiner*—Margaret G. Moore

(57) ABSTRACT

An ocular lens material comprising a siloxane-containing polymer obtained by polymerizing a monomer mixture containing (A) a siloxane macromonomer having at least two active unsaturated groups and a number average molecular weight of 2,000 to 100,000; and (B) a vinyl ester of lower fatty acid as essential components. An ocular lens material comprising a polymer obtained by saponification of the siloxane-containing polymer. Processes for producing the ocular lens materials. The ocular lens materials are excellent not only in lipid-stain resistance, wettability and oxygen permeability, but also in flexibility, particularly, shape recovery at the same time.

21 Claims, No Drawings

OCULAR LENS MATERIALS AND PROCESS FOR PRODUCING THE SAME

TECHNICAL FIELD

The present invention relates to an ocular lens material and a process for producing the same. More particularly, the present invention relates to an ocular lens material suitably used for, for example, soft contact lens and soft intraocular lens, which is excellent not only in lipid-stain resistance, wettability and oxygen permeability, but also in flexibility, particularly, shape recovery at the same time, and a process for producing the ocular lens material.

BACKGROUND ART

Recently, consumer's demands for contact lenses, for example, are directed to a soft contact lens with high oxygen permeability, and for intraocular lenses, for example, a foldable intraocular lens. For these reasons, various materials having properties such as high oxygen permeability and excellent flexibility in particular are suggested.

For instance, a contact lens comprising a copolymer obtained by polymerizing siloxanyl (meth)acrylate and vinyl ester is disclosed in Japanese Unexamined Patent Publication No. 163811/1988, and a contact lens comprising a copolymer obtained by polymerizing siloxanyl (meth)acrylate, a vinyl ester, and vinyl (meth)acrylate and/or allyl (meth)acrylate is disclosed in Japanese Unexamined Patent Publication No. 301919/1988.

However, it cannot be said that these contact lenses are excellent in flexibility taking the monomer mixture into account though all of them have high oxygen permeability and excellent stain resistance.

In addition to the above, a water-containing contact lens obtained by saponifying a polymer comprising a (meth)acrylate polymer, which has at least one polymerizable group on average, a vinyl monomer, a vinyl ester of fatty acid and a crosslinkable monomer, is disclosed in Japanese Unexamined Patent Publication No. 102471/1994, and a silicone-containing hydrogel material formed from a polymer prepared by using a monomer mixture comprising a polysiloxane pre-polymer, a bulk polysiloxanylalkyl (meth)acrylate monomer and a hydrophilic monomer is disclosed in Japanese Unexamined Patent Publication No. 508063/1995. Also, in International Publication No. WO 97/09169, an ocular lens material obtained by hydrating, by using a water-soluble organic solvent, a polymer prepared by solution polymerization of a polymerizable silicon-containing compound and/or a polymerizable fluorine-containing compound, hydroxyalkyl (meth)acrylate, and a cross-linked compound is disclosed.

However, though these contact lenses and materials have properties such as high oxygen permeability, lipid-stain resistance and wettability, they only have one or a plurality of such properties, and do not show flexibility, particularly shape recovery, which is one of the important properties required for an ocular lens material, in particular, a soft ocular lens material.

As mentioned above, ocular lens materials having not only high oxygen permeability, excellent lipid-stain resistance and superior wettability but also shape recovery at the same time have not been provided yet. Accordingly, development of such materials as the above has been expected.

The present invention has been carried out from the viewpoint of the above prior arts. An object of the present invention is to provide an ocular lens material which has not only high oxygen permeability, excellent wettability and superior lipid-stain resistance, but also flexibility, particularly shape recovery at the same time, and an easy process for producing the ocular lens material.

DISCLOSURE OF INVENTION

The present invention relates to (1) an ocular lens material comprising a siloxane-containing polymer obtained by polymerizing a monomer mixture containing
  (A) a siloxane macromonomer having at least two active unsaturated groups and a number average molecular weight of 2,000 to 100,000; and
  (B) a vinyl ester of lower fatty acid as essential components;

(2) an ocular lens material comprising a polymer prepared by saponifying a siloxane-containing polymer obtained by polymerizing a monomer mixture containing
  (A) a siloxane macromonomer having at least two active unsaturated groups and a number average molecular weight of 2,000 to 100,000; and
  (B) a vinyl ester of lower fatty acid as essential components; and (3) a process for producing the above ocular lens material, characterized by preparing a siloxane-containing polymer by polymerization of a monomer mixture containing
  (A) a siloxane macromonomer having at least two active unsaturated groups and a number average molecular weight of 2,000 to 100,000; and
  (B) a vinyl ester of lower fatty acid as essential components; and then
subjecting said siloxane-containing polymer to saponification.

BEST MODE FOR CARRYING OUT THE INVENTION

The ocular lens material of the present invention, hereinafter referred to as an ocular lens material I, comprises a siloxane-containing polymer obtained by polymerizing a monomer mixture containing (A) a siloxane macromonomer having at least two active unsaturated groups and a number average molecular weight of 2,000 to 100,000; and (B) a vinyl ester of lower fatty acid as essential components.

The siloxane macromonomer (A) is a component which mainly imparts flexibility as typified by shape recovery and mechanical strength to the ocular lens material I.

The active unsaturated group in the siloxane macromonomer (A) is an active unsaturated group which can be subjected to radical polymerization. Examples of the active unsaturated group are (meth)acryloyl group, vinyl group, allyl group, (meth)acryloyloxy group, vinyl carbamate group and the like. Among these, acryloyloxy group and vinyl group are preferable from the viewpoint that they can impart excellent flexibility to the ocular lens material I and copolymerizability with other monomers is excellent.

In the instant specification, "(meth)acryl—" means "acryl— and/or methacryl—".

It is desired that a number average molecular weight of the siloxane macromonomer (A) is at least 2,000, preferably at least 2,500 and more preferably at least 3,000 in order to impart excellent flexibility to the ocular lens material I without increasing hardness extremely. Also, it is desired that a number average molecular weight of the siloxane macromonomer (A) is at most 100,000, preferably at most 50,000, more preferably at most 10,000 not to make shape recovery inferior though the ocular lens material I becomes softened.

As the siloxane macromonomer (A), for example, the macromonomer of dialkyl siloxane having an active unsaturated group described in U.S. Pat. No. 4,189,546 specification can be used to obtain the aimed ocular lens material I.

Usually, many siloxane macromonomers are bad in wettability and relatively lack mechanical strength when each of the macromonomers is homopolymerized. Accordingly, as the siloxane macromonomer (A) used in the present invention, a siloxane macromonomer having a urethane group represented by the formula:

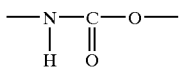

in the macromonomer structure is preferable in order to improve wettability.

When the siloxane macromonomer (A) contains the above urethane group, suitable mechanical strength and excellent wettability can be imparted to the ocular lens material I. It is desired that the number of the urethane group in the siloxane macromonomer (A) is at least 2, preferably at least 4 on average in order to impart sufficient mechanical strength and wettability. On the other hand, when too many urethane groups are introduced, flexibility of the ocular lens material I decreases. Therefore, it is desired that the average number of the urethane group in the siloxane macromonomer (A) is at most 20, preferably at most 14.

In the present invention, the macromonomer to which hydrophilic parts are introduced at the both ends of the siloxane structure described in U.S. Pat. No. 4,495,361 specification or U.S. Pat. No. 5,807,944 specification can also be used as the siloxane macromonomer (A) in order to obtain the ocular lens material I whose flexibility, particularly shape recovery, is improved.

In the present invention, as the siloxane macromonomer (A), a macromonomer represented by the formula (I-1) is preferably used:

$$A^1-(-U^1-S^1-)_n-U^2-S^2-U^3-A^2 \qquad (I\text{-}1)$$

wherein each of $A^1$ and $A^2$ is independently an active unsaturated group, an active unsaturated group having an alkylene group having 1 to 20 carbon atoms or an active unsaturated group having an alkylene glycol group having 1 to 20 carbon atoms;

$U^1$ is a diurethane type group which contains urethane bonds formed with adjacent $A^1$ and adjacent $S^1$ on both sides or which contains urethane bonds with adjacent two $S^1$ on both sides;

$U^2$ is a diurethane type group which contains urethane bonds formed with adjacent $A^1$ and adjacent $S^2$ on both sides or which contains urethane bonds with adjacent $S^1$ and adjacent $S^2$ on both sides;

$U^3$ is a diurethane type group which contains urethane bonds formed with adjacent $S^2$ and adjacent $A^2$ on both side;

each of $S^1$ and $S^2$ is independently a group represented by the formula:

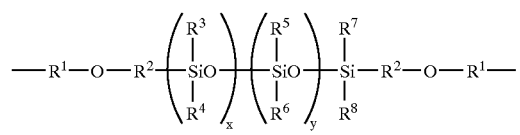

wherein each of $R^1$ and $R^2$ is independently an alkylene group having 1 to 20 carbon atoms, each of $R^3$, $R^4$, $R^5$, $R^6$, $R^7$ and $R^8$ is independently a linear, branched or cyclic alkyl group having 1 to 20 carbon atoms, which may be substituted with a fluorine atom, or a group represented by the formula:

$$A^3-U^4-R^1-O-R^2-$$

in which $A^3$ is an active unsaturated group, an active unsaturated group having an alkylene group having 1 to 20 carbon atoms or an active unsaturated group having an alkylene glycol group having 1 to 20 carbon atoms, $U^4$ is a urethane type group which contains urethane bonds formed with adjacent $A^3$ and adjacent $R^1$ on both sides, and each of $R^1$ and $R^2$ is the same as above, x is an integer of 1 to 1500, y is 0 or an integer of 1 to 1499, and x+y is an integer of 1 to 1500;

n is 0 or an integer of 1 to 10;

or a macromonomer represented by the following formula (I-2) is preferably used:

$$B^1-S^3-B^1 \qquad (I\text{-}2)$$

wherein $B^1$ is an active unsaturated group having urethane bond; and $S^3$ is a group represented by the formula:

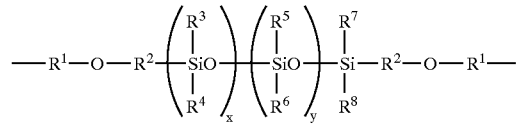

wherein each of $R^1$ and $R^2$ is independently an alkylene group having 1 to 20 carbon atoms, each of $R^3$, $R^4$, $R^5$, $R^6$, $R^7$ and $R^8$ is independently a linear, branched or cyclic alkyl group having 1 to 20 carbon atoms, which may be substituted with fluorine atom, or a group represented by the formula:

$$A^3-U^4-R^1-O-R^2-$$

in which $A^3$ is an active unsaturated group, an active unsaturated group having an alkylene group having 1 to 20 carbon atoms or an active unsaturated group having an alkylene glycol group having 1 to 20 carbon atoms, $U^4$ is a urethane type group which contains urethane bonds formed with adjacent $A^3$ and adjacent $R^1$ on both sides, and each of $R^1$ and $R^2$ is the same as above, x is an integer of 1 to 1500, y is 0 or an integer of 1 to 1499, and x+y is an integer of 1 to 1500.

In the formula (I-1), examples of the active unsaturated group represented by $A^1$ and $A^2$ are (meth)acryloyl group, vinyl group, allyl group, (meth)acryloyloxy group, vinyl carbamate group and the like as mentioned above. Among them, acryloyloxy group and vinyl group are preferable and acryloyloxy group is particularly preferable, since more excellent flexibility can be imparted to the ocular lens material I and copolymerizability with other monomers is excellent.

When the above active unsaturated group has an alkylene group or an alkylene glycol group, it is desired that the number of carbon atoms of the alkylene group or the alkylene glycol group is 1 to 20, preferably 1 to 10.

In the formula (I-1), as to the group $S^1$ or $S^2$ represented by the formula:

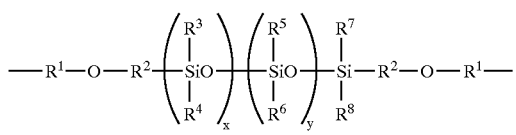

wherein each of $R^1$, $R^2$, $R^3$, $R^4$, $R^5$, $R^6$, $R^7$, $R^8$, x and y is the same as above, each of $R^1$ and $R^2$ is preferably an alkylene group having 1 to 5 carbon atoms, and each of $R^3$, $R^4$, $R^5$, $R^6$, $R^7$ and $R^8$ is preferably an alkyl group having 1 to 5 carbon atoms. $A^3$ in the formula: $A^3$—$U^4$—$R^1$—O—$R^2$—, which represents $R^3$, $R^4$, $R^5$, $R^6$, $R^7$ or $R^8$, is the same active unsaturated group as the above-exemplified one. When the active unsaturated group has an alkylene group or an alkylene glycol group, it is desired that the number of carbon atoms of the alkylene group or the alkylene glycol group is 1 to 20, preferably 1 to 10 carbon atoms. In addition, it is desired that x is an integer of 1 to 500, y is 0 or an integer of 1 to 499, and x+y is an integer of 1 to 500.

In the formula (I-1), it is desired that n is 0 or an integer of 1 to 5.

In the formula (I-2), examples of the active unsaturated group having urethane bond, represented by $B^1$ are (meth) acryloylisocyanate group, (meth)acryloyloxyisocyanate group, allylisocyanate group, vinylbenzylisocyanate group and the like. The group represented by $S^3$ in the formula (I-2) is the same as the group represented by $S^1$ or $S^2$ in the above formula (I-1).

Among the above macromonomers, because flexibility such as shape recovery and mechanical strength can be greatly imparted to the lens material, a macromonomer represented by the formula:

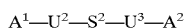

wherein each of $A^1$, $A^2$, $U^2$, $U^3$ and $S^2$ is the same as above; and a macromonomer represented by the formula:

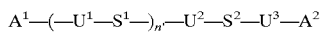

wherein each of $A^1$, $A^2$, $U^1$, $U^2$, $U^3$, $S^1$ and $S^2$ is the same as above, and n' is an integer of 1 to 4, are preferable. In particular, a macromonomer represented by the formula:

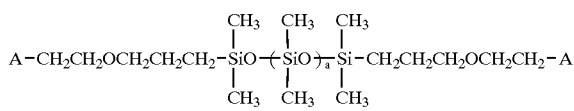

wherein A is a group represented by the formula:

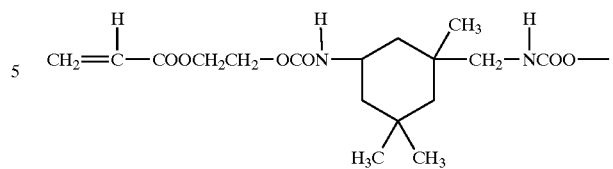

and a is an integer of 20 to 50, is preferable.

The above vinyl ester of lower fatty acid (B) is a component which mainly imparts shape recovery to the ocular lens material I and hydrophilic property to the ocular lens material II according to the saponification mentioned below.

Typical examples of the vinyl ester of lower fatty acid (B) is a compound represented by the formula (II):

wherein R is hydrogen atom or an alkyl group having 1 to 15 carbon atoms, which may be substituted with a halogen atom. Concrete examples of the compound are vinyl formate, vinyl acetate, vinyl propionate, vinyl butyrate, vinyl pivalate, vinyl versatate, vinyl laurate, vinyl stearate, vinyl monochloroacetate, vinyl monofluoroacelate, vinyl trichloroacetate, vinyl trifluoroacetate and the like. These can be used alone or in a mixture thereof.

Among the above vinyl esters of lower fatty acid (B), because shape recovery and hydrophilic property can be greatly imparted to the lens material, vinyl acetate, vinyl propionate and vinyl pivalate are preferable. In particular, vinyl acetate is preferable.

The siloxane-containing polymer which constitutes the ocular lens material I of the present invention is prepared by polymerizing the monomer mixture containing the siloxane macromonomer (A) and the vinyl ester of lower fatty acid (B) as essential components. The monomer mixture can also contain, for instance, a silicon-containing monomer (C).

The above silicon-containing monomer (C) is preferably used since it is a component which mainly imparts oxygen permeability and further, flexibility, particularly shape recovery, to the ocular lens material I.

Typical examples of the silicon-containing monomer (C) are a silicon-containing (meth)acrylate such as pentamethyldisiloxanylmethyl (meth)acrylate, trimethylsiloxydimethylsilylpropyl (meth)acrylate, methylbis(trimethylsiloxy) silylpropyl (meth)acrylate, tris(trimethylsiloxy)silylpropyl (meth)acrylate, mono[methylbis(trimethylsiloxy)siloxy]bis (trimethylsiloxy)silylpropyl (meth)acrylate, tris[methylbis (trimethylsiloxy)siloxy]silylpropyl (meth)acrylate, trimethylsilylmethyl (meth)acrylate, trimethylsilylpropyl (meth) acrylate, methylbis(trimethylsiloxy) silylethyltetramethyldisiloxanylmethyl (meth)acrylate, tetramethyltriisopropylcyclotetrasiloxanylpropyl (meth) acrylate, tetramethyltriisopropylcyclotetrasiloxybis (trimethylsiloxy)silylpropyl (meth)acrylate or trimethylsiloxydimethylsilylpropyl (meth)acrylate; a silicon-containing styrene derivative represented by the formula:

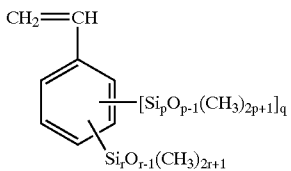

wherein p is an integer of 1 to 15, q is 0 or 1 and r is an integer of 1 to 15, such as tris(trimethylsiloxy)silylstyrene, methylbis(trimethylsiloxy)silylstyrene, dimethylsilylstyrene, trimethylsilylstyrene, tris (trimethylsiloxy)siloxanyldimethylsilylstyrene, [methylbis (trimethylsiloxy)siloxanyl]dimethylsilylstyrene, pentamethyldisiloxanylstyrene, heptamethyltrisiloxanylstyrene, nonamethyltetrasiloxanylstyrene, pentadecamethylheptasiloxanylstyrene, heneicosamethyldecasiloxanylstyrene, heptacosamethyltridecasiloxanylstyrene, hentriacontamethylpentadecasiloxanylstyrene, trimethylsiloxypentamethyldisiloxymethylsilylstyrene, tris (pentamethyldisiloxy)silylstyrene, [tris(trimethylsiloxy) siloxanyl]bis(trimethylsiloxy)silylstyrene, methylbis (heptamethyltrisiloxy)silylstyrene, tris[methylbis (trimethylsiloxy)siloxy]silylstyrene, trimethylsiloxybis[tris (trimethylsiloxy)siloxy]silylstylene, heptakis (trimethylsiloxy)trisiloxanylstyrene, tris[tris (trimethylsiloxy)siloxy]silylstyrene, [tris(trimethylsiloxy) hexamethyltetrasiloxyl][tris(trimethylsiloxy)siloxy] trimethylsiloxysilylstyrene, nonakis(trimethylsiloxy) tetrasiloxanylstyrene, methylbis(tridecamethylhexasiloxy) silylstyrene, heptamethylcyclotetrasiloxanylstyrene, heptamethylcyclotetrasiloxybis(trimethylsiloxy)silylstyrene or tripropyltetramethylcyclotetrasiloxanylstyrene; and the like. These can be used alone or in admixture thereof.

Among the above silicon-containing monomers (C), because high oxygen permeability and flexibility, in particular, shape recovery can be greatly imparted to the ocular lens material I at the same time, the silicon-containing (meth)acrylate is preferable. In particular, tris (trimethylsiloxy)silylpropyl acrylate is preferable.

Furthermore, the monomer mixture can also contain, for instance, a fluorine-containing monomer (D), in addition to the siloxane macromonomer (A), the vinyl ester of lower fatty acid (B) and the silicon-containing monomer (C).

The fluorine-containing monomer (D) is a component which mainly imparts oxygen permeability and flexibility to the ocular lens material I, improving lipid-stain resistance at the same time.

Typical examples of the fluorine-containing monomer (D) are 2,2,2-trifluoroethyl (meth)acrylate, 2,2,3,3-tetrafluoropropyl (meth)acrylate, 2,2,3,3-tetrafluoro-t-pentyl (meth)acrylate, 2,2,3,4,4,4-hexafluorobutyl (meth)acrylate, 2,2,3,4,4,4-hexafluoro-t-hexyl (meth)acrylate, 2,3,4,5,5,5-hexafluoro-2,4-bis(trifluoromethyl)pentyl (meth)acrylate, 2,2,3,3,4,4-hexafluorobutyl (meth)acrylate, 2,2,2,2',2',2'-hexafluoroisopropyl (meth)acrylate, 2,2,3,3,4,4,4-heptafluorobutyl (meth)acrylate, 2,2,3,3,4,4,5,5-octafluoropentyl (meth)acrylate; a fluoroalkyl (meth) acrylate represented by the formula:

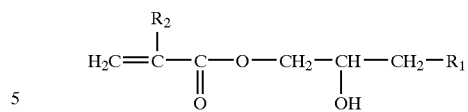

wherein $R_1$ is a fluoroalkyl group having 3 to 15 carbon atoms and $R_2$ is hydrogen atom or a methyl group, such as 3-perfluorobutyl-2-hydroxypropyl (meth)acrylate, 3-perfluorohexyl-2-hydroxypropyl (meth)acrylate, 3-perfluorooctyl-2-hydroxypropyl (meth)acrylate, 3-(perfluoro-3-methylbutyl)-2-hydroxypropyl (meth) acrylate, 3-(perfluoro-5-methylhexyl)-2-hydroxypropyl (meth)acrylate or 3-(perfluoro-7-methyloctyl)-2-hydroxypropyl (meth)acrylate; and the like.

Among them, fluoroalkyl acrylate is preferable since flexibility can be greatly imparted to the ocular lens material I particularly out of oxygen permeability, flexibility and lipid-stain resistance.

Usually, many fluorine-containing compounds can impart oxygen permeability and lipid-stain resistance to a material, but are bad in wettability. To the contrary, a fluoroalkyl acrylate having a hydroxyl group represented by the formula:

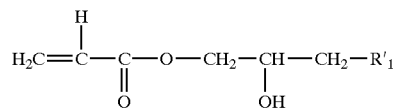

wherein $R'_1$ is a perfluoroallyl group having 3 to 15, preferably 3 to 8, more preferably 4 to 6 carbon atoms is particularly preferable from the viewpoint that flexibility and wettability can be imparted to the ocular lens material I without lacking oxygen permeability and lipid-stain resistance.

The proportion of the siloxane macromonomer (A), the vinyl ester of lower fatty acid (B) and the silicon-containing monomer (C) used as occasion demands is preferably defined as mentioned below. That is, in order to impart sufficient flexibility, mechanical strength and oxygen permeability to the ocular lens material I, it is desired that the ratio of the total weight of the siloxane macromonomer (A) and the silicon-containing monomer (C) to the weight of the vinyl ester of lower fatty acid (B), the total weight of (A) and (C)/the weight of (B), that is, when the silicon-containing monomer (C) is not used, the weight of (A)/the weight of (B), is at least 30/70, preferably at least 50/50. In order to impart sufficient shape recovery and hydrophilic property to the ocular lens material I, it is desired that the above ratio is at most 90/10, preferably at most 80/20.

When the silicon-containing monomer (C) is used, the ratio of the weight of the siloxane macromonomer (A) to the weight of the silicon-containing monomer (C), the weight of (A)/the weight of (C), is preferably defined as mentioned below. That is, in order to impart sufficient mechanical strength to the ocular lens material I without lowering shape recovery, it is desired that the weight of (A)/the weight of (C) is at least 20/80, preferably at least 25/75. In order to impart sufficient oxygen permeability to the ocular lens material I, it is desired that the above ratio is at most 90/10, preferably at most 80/20.

The proportion of the siloxane macromonomer (A) and the vinyl ester of lower fatty acid (B), and the silicon-containing monomer (C) and the fluorine-containing monomer (D) which are used as occasion demands is preferably defined as mentioned below. That is, in order to impart effects from the siloxane macromonomer (A), the vinyl ester of lower fatty acid (B) and the silicon-containing monomer (C) sufficiently to the ocular lens material I, it is desired that the ratio of the total weight of siloxane macromonomer (A), the vinyl ester of lower fatty acid (B) and the silicon-containing monomer (C) to the weight of the fluorine-containing monomer (D), the total weight of (A), (B) and (C)/the weight of (D), is at least 20/80, preferably at least 40/60. In order to impart sufficient lipid-stain resistance in particular to the ocular lens material I, it is desired that the above ratio is at most 90/10, preferably at most 85/15.

As occasion demands, the monomer mixture can also contain a crosslinkable compound (E) having at least two polymerizable groups.

The above crosslinkable compound (E) is a component which mainly imparts optical properties such as transparency to the ocular lens material I and further improves mechanical strength thereof so that the ocular lens material I can be used as a lens material.

Typical examples of the crosslinkable compound (E) are ethylene glycol di(meth)acrylate, diethylene glycol di(meth)acrylate, triethylene glycol di(meth)acrylate, propylene glycol di(meth)acrylate, dipropylene glycol di(meth)acrylate, allyl (meth)acrylate, vinyl (meth)acrylate, trimethylolpropane tri(meth)acrylate, methacryloyloxydiethyl acrylate, divinylbenzene, diallyl phthalate, diallyl adipate, diethylene glycol diallyl ether, triallylisocyanurate, α-methylene-N-vinylpyrrolidone, 4-vinylbenzyl (meth)acrylate, 3-vinylbenzyl (meth)acrylate, 2,2-bis(p-(meth)acryloyloxyphenyl)hexafluoropropane, 2,2-bis(m-(meth)acryloyloxyphenyl)hexafluoropropane, 2,2-bis(o-(meth)acryloyloxyphenyl)hexafluoropropane, 1,4-bis(2-(meth)acryloyloxyhexafluoroisopropyl)benzene, 1,3-bis(2-(meth)acryloyloxyhexafluoroisopropyl)benzene, 1,2-bis(2-(meth)acryloyloxyhexafluoroisopropyl)benzene, 1,4-bis(2-(meth)acryloyloxyisopropyl)benzene, 1,3-bis(2-(meth)acryloyloxyisopropyl)benzene, 1,2-bis(2-(meth)acryloyloxyisopropyl)benzene and the like. These can be used alone or in admixture thereof.

Among the above crosslinkable compounds (E), because optical property and mechanical strength can be greatly imparted to the ocular lens material I and handling is easy, ethylene glycol di(meth)acrylate, diethylene glycol di(meth)acrylate, diallyl adipate and diethylene glycol diallyl ether are preferable. In particular, ethylene glycol di(meth)acrylate and diethylene glycol diallyl ether are preferable.

In order to impart sufficient optical property and mechanical strength to the ocular lens material I, it is desired that the amount of the crosslinkable compound (E) in the monomer mixture is at least 0.01% by weight, preferably at least 0.05% by weight. In order to remove fear that flexibility of the ocular lens material I is lowered although mechanical strength is imparted to the ocular lens material I, it is desired that the amount of the crosslinkable compound (E) in the monomer mixture is at most 15% by weight, preferably at most 10% by weight.

The above monomer mixture may further contain an ultraviolet-ray absorbing agent in order to improve ultraviolet-ray absorbability of the ocular lens material I.

Examples of the ultraviolet-ray absorbing agent are a benzotriazole ultraviolet-ray absorbing agent such as 2-(2'-hydroxy-5'-methacryloxyethyleneoxy-t-butylphenyl)-5-methylbenzotriazole or a compound represented by the formula (III):

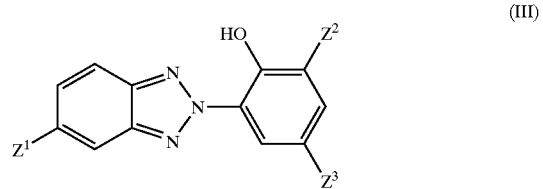

wherein $Z^1$ is hydrogen atom, a halogen atom such as chlorine atom, bromine atom or iodine atom, an alkyl group having 1 to 6 carbon atoms or an alkoxyl group having 1 to 6 carbon atoms, and each of $Z^2$ and $Z^3$ is independently hydrogen atom or an alkyl group having 1 to 6 carbon atoms, such as 2-(2'-hydroxy-5'-methylphenyl)benzotriazole, 5-chloro-2-(3'-t-butyl-2'-hydroxy-5'-methylphenyl)benzotriazole or 2-(5-chloro-2H-benzotriazole-2-yl)-6-(1,1-dimethyl)-4-methylphenol; a benzophenone ultraviolet-ray absorbing agent such as 2-hydroxy-4-methoxybenzophenone or 2-hydroxy-4-octoxybenzophenone; a salicylic acid derivative ultraviolet-ray absorbing agent; a hydroxyacetophenone derivative ultraviolet-ray absorbing agent; and the like. Among them, the benzotriazole ultraviolet-ray absorbing agent is preferable from the viewpoint of ultraviolet-ray absorbability. In particular, the compound represented by the formula (III), such as 2-(5-chloro-2H-benzotriazole-2-yl)-6-(1,1-dimethyl)-4-methylphenol is preferable.

The above ultraviolet-ray absorbing agent may or may not have a polymerizable group, and is not particularly limited.

It is desired that the amount of the above ultraviolet-ray absorbing agent in the monomer mixture is at least 0.01% by weight, preferably at least 0.05% by weight in order to impart sufficient ultraviolet-ray absorbability to the ocular lens material I. Also, it is desired that the amount is at most 5% by weight, more preferably at most 3% by weight in order to prevent relative decrease in other properties and induction of polymerization inhibition caused by excessive addition.

In order to produce the ocular lens material I of the present invention, a siloxane-containing polymer can be prepared by polymerizing the above monomer mixture.

In preparing the above siloxane-containing polymer, a radical polymerization initiator, a photo sensitizer and the like are usually added first to the monomer mixture obtained by adjusting kind and amount of monomers. They are added in accordance with a radical polymerization method such as a thermal polymerization method or a photo polymerization method mentioned below, wherein radical generated in an active unsaturated group is subjected to polymerization reaction.

Typical examples of the radical polymerization initiator are a thermal polymerization initiator such as azobisisobutyronitrile, azobisdimethylvaleronitrile, benzoyl peroxide, t-butyl hydroperoxide, cumene peroxide; a benzoin photo polymerization initiator such as methylorthobenzoyl benzoate, methylbenzoyl formate, benzoin methyl ether, benzoin ethyl ether, benzoin isopropyl ether, benzoin isobutyl ether or benzoin-n-butyl ether; a phenone photo polymerization initiator such as 2-hydroxy-2-methyl-1-phenylpropane-1-one, p-isopropyl-a-hydroxyisobutylphenone, p-t-butyltrichloroacetophenone, 2,2-dimethoxy-2-phenylacetophenone, α,α-dichloro-4-phenoxyacetophenone or N,N-tetraethyl-4,4-diaminobenzophenone; 1-hydroxycyclohexyl phenyl ketone; 1-phenyl-1,2-propanedione-2-(o-ethoxycarbonyl) oxime; a thioxanthone photo polymerization initiator such as 2-chlorothioxanthone or 2-methylthioxanthone; dibenzosvarron; 2-ethylanthraquinone; benzophenone acrylate; benzophenone; benzyl; and the like.

The photo sensitizer is not activated independently by irradiation of ultraviolet-ray. However, when used together with a photo initiator, the photo sensitizer effects as a promotor and show more excellent effects than the photo initiator alone. Examples of the photo sensitizer are 1,2-benzoanthraquinone; an amine compound such as n-butylamine, di-n-butylamine or triethylamine; tri-n-butylphosphine; allylthiourea; s-benzylisothiuronium-p-toluenesulfinate; diethylaminoethyl methacrylate; and the like.

The radical polymerization initiator and the photo sensitizer can be suitably selected and used alone or in admixture thereof. It is desired that the amount thereof is about 0.002 to 2 parts by weight (hereinafter referred to as "part(s)"), preferably about 0.01 to 1 part, based on 100 parts of the total amount of the monomer mixture.

In the radical polymerization method, only a radical polymerization initiator and a photo sensitizer may be used for polymerization of the monomer mixture. However, a diluent can be also used, for instance, to improve compatibility of each monomer.

Typical examples of the diluent are an alcohol such as methanol, ethanol, propanol, butanol, pentanol or hexanol; a ketone such as acetone or methyl ethyl ketone; an ether such as diethyl ether or tetrahydrofuran; and the like. These can be used alone or in admixture thereof.

Among the diluents, an alcohol having 1 to 6 carbon atoms is preferable since the monomer mixture gains excellent solubility. In particular, n-propanol, n-butanol and n-pentanol are preferable.

The monomer mixture is admixed with the diluent according to the following proportion. That is, in order to dissolve the monomer mixture in the diluent sufficiently, it is desired that the weight ratio of the monomer mixture to the diluent, the monomer mixture/the diluent, is at most 90/10, preferably at most 80/20. In order to remove fear that the aimed polymer becomes cloud in white to lower optical property and the polymer lacks mechanical strength, it is desired that the above weight ratio is at least 30/70, preferably at least 50/50.

The ocular lens material I can be prepared by means of every conventional method. However, from the viewpoint of achieving maximum benefit from the properties of the ocular lens material I, it is particularly preferable to produce a lens by preparing a siloxane-containing polymer according to polymerization reaction after injecting the above monomer mixture and, if necessary, the above diluent into a mold composed of two parts, one part corresponding to the front shape of a lens, such as, a contact lens or an intraocular lens, and the other part corresponding to the back shape of the lens, and sealing the mold. In case of producing an intraocular lens, a mold having a shape corresponding to a one-piece intraocular lens in which an optic and haptics are united with each other may be used. Also, a mold having a shape corresponding to the optic and a mold having a shape corresponding to the haptics may be used.

After a monomer mixture and, if necessary, a diluent are injected into the mold, polymerization reaction is carried out to give a siloxane-containing polymer. Any usual method can be employed for the polymerization without particular limitation.

The methods for the polymerization are, for instance, a thermal polymerization method, wherein a mixture of a monomer mixture containing the above radical polymerization initiator and, if necessary, a diluent, is heated at about 30° C. to 60° C. for several hours to several 10 hours to polymerize the mixture, and then the temperature of reaction system is gradually increased to about 120° C. to 140° C. over several hours to ten and several hours to complete the polymerization; a photo polymerization method, wherein the above mixture is irradiated with light ray such as ultraviolet-ray, which has wavelength corresponding to absorption band of activation of the radical polymerization initiator and then, the monomer mixture is polymerized; and a combination method of thermal polymerization and photo polymerization.

When the thermal polymerization method is carried out, the above mixture can be heated in a thermostat container or a thermostat room, and can be irradiated with electromagnetic wave such as microwave. The temperature of the mixture may be increased stepwise. When the photo polymerization method is carried out, the photo sensitizer may be further added to the mixture.

The thus-obtained siloxane-containing polymer is put out from the mold to give the ocular lens material I of the present invention.

The above ocular lens material I can be subjected to mechanical process such as cutting process or polishing process as occasion demands.

The above ocular lens material I has excellent properties sufficient and suitable for an ocular lens material. However, the above siloxane-containing polymer is subjected to saponification to obtain a material whose wettability is further improved.

That is, the ocular lens material of the present invention, hereinafter referred to as ocular lens material II, comprises a polymer prepared by saponifying a siloxane-containing polymer obtained by polymerizing a monomer mixture containing (A) a siloxane macromonomer having at least two active unsaturated groups and a number average molecular weight of 2,000 to 100,000; and (B) a vinyl ester of lower fatty acid as essential components. The process of the present invention is characterized by the above saponification.

The saponification in the present invention is to form vinyl alcohol as mentioned below by subjecting units derived from the vinyl ester of lower fatty acid (B) in the polymer, which can decompose by saponification, to alkali treatment with an alkaline compound or to acid treatment with, for instance, sulfuric acid according to the conventionally known saponification method of polyvinyl ester. In saponification by the acid treatment, however, there are defects that saponification speed is late, uniform saponification is difficult and that side reaction occurs. For these reasons, saponification by the alkali treatment is preferred. By saponification, hydrophilic property, in other words surface wettability, can be imparted to the ocular lens material II without much increase of water content.

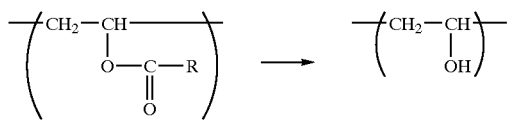

wherein R is the same as the above.

Examples of the alkaline compound used for the alkali treatment are ammonia, an alkaline metal hydroxide, an alkaline earth metal hydroxide and the like. Concrete examples of the alkaline compound are ammonium hydroxide, sodium hydroxide, potassium hydroxide, calcium hydroxide and the like. Because most alkaline compounds are solids, it is preferred that these alkaline compounds are dissolved in water, an alcohol, an ether or the like to give an alkaline solution and the alkaline solution is used for saponification.

Examples of the alcohol are methanol, ethanol, propanol, butanol and the like. Examples of the ether are diethyl ether, tetrahydrofuran and the like.

Among the alkaline solutions of alkaline compound used for saponification, those obtained from an alcohol are preferable. In order to carry out saponification efficiently, a methanol aqueous solution of sodium hydroxide having a concentration of 0.01 to 1 mol/L is more preferable. In particular, a methanol aqueous solution of sodium hydroxide, in which the volume ratio of methanol to water, methanol/water, is 30/70 to 90/10, is preferable.

An ocular lens material can be subjected to dyeing in case where saponification is carried out by alkali treatment in the present invention.

Specifically, a siloxane-containing polymer is prepared as mentioned above, then immersed and swollen in a mixture obtained by dispersing, or dissolving a dye in an organic solvent such as methanol, ethanol or 2-propanol, and non-reacted residual monomers in the siloxane-containing polymer are eluted while the dye is dispersed in the polymer at the same time. The dye can be fixed to the siloxane-containing polymer in subsequent saponification by alkali treatment.

There is no particular limitation for the above dye. Preferable examples thereof are, for example, reactive dyes such as C. I. Reactive Black 5, C. I.: standing for "Color Index", hereinafter referred to as the same, C. I. Reactive Blue 21, C. I. Reactive Orange 78, C. I. Reactive Yellow 15, C. I. Reactive Blue 4, C. I. Reactive Red 11, C. I. Reactive Yellow 86, C. I. Reactive Blue 163, C. I. Reactive Red 180, and the like. The amount of the dye is not particularly limited as long as it is used in such an amount that sufficient dyeing of the ocular lens material II can be achieved.

The siloxane-containing polymer is subjected to saponification by immersing the polymer in the above alkaline solution or the above solution of acidic compound.

The temperature in saponification is not particularly limited. In general, it is desired that the temperature is about 0° C. to about 100° C., preferably about 10° C. to about 70° C.

The treatment time for saponification, which is not determined as a whole, can be changed depending on kind of alkaline compound and acidic compound, concentration of alkaline compound and acidic compound, or temperature of saponification. However, it is desired that the treatment time is at least 0.1 hour, preferably at least 0.5 hour in order to improve hydrophilic property of the ocular lens material II effectively. Also, it is desired that the treatment time is at most 30 hours, preferably at most 15 hours, in order to remove fears that an inappropriate material for an ocular lens is produced because the material becomes cloud in white to lower transparency, or because mechanical strength thereof is lowered, and that working efficiency is lowered due to extended treatment time.

The saponified polymer can be boiled in physiological saline (0.9% sodium chloride aqueous solution) for several hours.

Further, it is also possible to carry out the above saponification after photo-irradiation to the prepared siloxane-containing polymer in the present invention.

The ocular lens material II obtained by the saponification of alkali treatment after photo-irradiation to the siloxane-containing polymer has further increased surface wettability.

It is preferable to carry out photo-irradiation before the saponification to a siloxane-containing polymer as mentioned above, but there, is no particular limitation for the condition of the siloxane-containing polymer as long as the polymer is dried or swollen by an extraction solution employed for removing residual monomers during extraction process.

It is desired that light to be irradiated is ultraviolet ray having a wavelength of preferably at most 380 nm, more preferably at most 300 nm from the viewpoint of efficient improvement of wettability. It is particularly preferable to irradiate ultraviolet ray having a wavelength near 185 nm and ultraviolet ray having a wavelength near 250 nm simultaneously.

It is desired that the photo-irradiation time is 0.1 to 600 minutes, preferably 1 to 60 minutes from the viewpoint of efficient improvement of wettability without affecting productivity to produce a desired ocular lens from the ocular lens material II.

Either of the above steps may precede when both of the steps are employed together, one step being such that a siloxane-containing polymer is immersed and swollen in a mixture obtained by dispersing, or dissolving, a dye in an organic solvent to elute residual monomers in the siloxane-containing polymer which did not react while the dye is dispersed in the polymer at the same time, and the other step being such that the siloxane-containing polymer is irradiated with photo. When the photo-irradiation step is carried out after the elution step, light may be irradiated after a sample is dried for increased efficiency of photo-irradiation.

The ocular lens material I of the present invention is most suitable for a soft ocular lens material in particular. This is because the ocular lens material I has excellent flexibility, particularly shape recovery, in addition to advantages of conventional soft ocular lens materials, such as high oxygen permeability, superior lipid-stain resistance and excellent wettability. The reason why a material excellent in shape recovery is suitable for a soft ocular lens material can be seen when a material inferior in shape recovery is taken into account. When used as a contact lens, a material inferior in shape recovery disturbs stable eyesight immediately after wearing lenses, causes uncomfortable feeling to patients during wearing lenses, and further, induces troubles in eyeball. Meanwhile, when an ocular lens material is used as a soft intraocular lens, the best advantage of the soft intraocular lens resides in the fact that incision of eyeball can be extremely small since the lens is foldable when inserted in the eye. However, when an ocular lens material is inferior in shape recovery, wide incision is therefore necessary because the material is difficult to fold. In addition, when shape recovery is inferior, it is difficult for a lens to recover its original shape after insertion in the eye and function as a lens is not achieved, resulting in lowering of eyesight. Accordingly, the ocular lens material I of the present invention is very suitable for an ocular lens material for the reason that it has excellent flexibility, particularly shape recovery, in addition to high oxygen permeability, superior lipid-stain resistance and excellent wettability.

Furthermore, in recent growing development of soft ocular lens materials with high oxygen permeability, use of a silicon-containing component is becoming essentially important for high oxygen permeability. However, though high oxygen permeability is imparted to the material, the material becomes extremely vulnerable to stain by lipid and inferior in hydrophilic property when used for an ocular lens because of high affinity of the silicon-containing component with a lipid component. Such characteristics are also inappropriate for an ocular lens material. On the contrary, the ocular lens material II of the present invention has not only high oxygen permeability and excellent flexibility as typified by shape recovery, but also excellent hydrophilic property, surface wettability in other words, and lipid stain resistance at the same time due to saponification, showing most suitable properties for an ocular lens material all together.

Next, the ocular lens material and the process for producing the same of the present invention are explained in detail, but the present invention is not limited thereto.

EXAMPLES 1 to 11 and COMPARATIVE EXAMPLES 1 to 6

Each of monomer mixtures shown in Tables 1 and 2 was mixed with 2-hydroxy-2-methyl-1-phenylpropane-1-one, as a polymerization initiator, in an amount of 0.2 part based on the monomer mixture. Then, the obtained mixture was injected into a mold having shape of a contact lens (made of polypropylene, corresponding to a contact lens having a diameter of 13.8 mm and a thickness of 0.2 mm).

Next, the mold was transferred into a constant temperature condition and photo polymerization was carried out by irradiating ultraviolet ray having a wavelength of 360 nm in about 1 mW/cm$^2$ to the content in the mold for an hour by using a mercury lamp to give a siloxane-containing polymer having shape of a contact lens.

The saponification of siloxane-containing polymers shown in Tables 1 and 2 was carried out by immersing the polymer in a 60% methanol aqueous solution containing 0.25 mol/L of sodium hydroxide whose temperature was 25° C. for six hours.

In Examples 6 and 10, a polymer having shape of a contact lens was obtained by directly saponifying the obtained siloxane-containing polymer, and a polymer having shape of a contact lens was obtained by irradiating ultraviolet ray having wavelength of 185 nm and ultraviolet ray having a wavelength of 254 nm for 10 minutes and then saponifying the obtained siloxane-containing polymer. These polymers to which ultraviolet ray was irradiated were used only for measuring dynamic contact angle mentioned below.

Oxygen permeability, shape recovery, flexibility in other words, surface wettability and lipid-stain resistance of polymers having shape of a contact lens in Examples 1 to 11 and Comparative Examples 1 to 6 were examined in accordance with the following method. The results are shown in Tables 3 to 5.
(a) Oxygen Permeability Dk values defined by ISO which stands for "International Organization for Standardization" were measured according to Fatt method.
(b) Shape Recovery (Flexibility)

The periphery of a polymer was fixed, while the center thereof was fixed to an apparatus for loading by using a spherical tool whose tip diameter was about 3 mm.

Stress was given to the fixed polymer up to about 20 g. This stress was removed and loss of repulsive force from the polymer was measured. The value $T_1$, the maximum load on the polymer, and then the value $T_2$, repulsive force from the polymer after 30 seconds were measured.

Using the measured values $T_1$ and $T_2$, shape recovery coefficient (%) was calculated on the basis of the following equation.

The larger the shape recovery coefficient is, the more inferior the shape recovery is. Particularly, when shape recovery coefficient is at least 18%, such material is inappropriate for an ocular lens, especially for a soft contact lens or a soft intraocular lens. In case of the soft contact lens, such material is not suitable because feeling for wearing becomes poor and unstable eyesight may be caused at wearing the lens immediately after the lens is handled by fingers. In case of the soft intraocular lens, such material is not suitable because trouble is caused for folding in operation and mark is left on the lens after insertion.

$$\text{Shape recovery coefficient (\%)} = \{(T_1 - T_2)/T_1\} \times 100$$

(a) Surface Wettability

After immersing the obtained polymer in saline for about 16 hours, the polymer was taken out and the surface thereof was observed with naked eyes. Evaluation was made according to the following criteria.
(Criteria for Evaluation)

⊚: Wettability for water is excellent on the whole. There is no repelling and cloud at all.

○: Repelling is partly observed, whereas there is no cloud and wettability is good.

Δ: Wettability for water is not good. Repelling and cloud is partly observed, or the material is clouded on the whole.

x: Wettability for water is poor. Repelling and cloud are observed.

In Examples 6 and 10 as well as Comparative Examples 1 and 4, the obtained polymer was cut into strip test pieces having a size of 5 mm wide, about 12 mm long and about 0.6 mm thick (which were prepared by using a punching knife to have the same width, obtained by changing an immersing solution from saline to distilled water; and whose thickness is measured for each piece). Dynamic contact angle was measured by using a dynamic contact angle measuring device DCA-322 made by CAHN Co., Ltd., equipped with cover glass, wherein distilled water for injection is used as a test solution. The measuring process is as follows.

First, the cover glass was used as a test piece to measure surface tension T of the test solution. Second, dynamic contact angle of each test piece was measured in accordance with measuring principle of Wilhelmy method under the following conditions.

Rate of immersion: 90 μm/s
Depth of immersion: 10 mm
Test weight: 500.0 mg
Test solution: distilled water for injection
Surface tension of test solution: the above measured value T
Cycle: 3 cycles As a result of the above measurement, the value at the second cycle was employed as dynamic contact angle (°).

Dynamic contact angle is an index for wettability of a polymer. A polymer whose dynamic contact angle is at least 120° has poor wettability and is inappropriate for an ocular lens material.

(b) Lipid-stain Resistance

The obtained polymer was put in a glass bottle containing 2 ml of an artificial tear lipid solution, a buffer solution of pH 7, which comprises 0.3 g of oleic acid, 0.3 g of linoleic acid, 4.0 g of tripalmitic acid, 1.0 g of cetyl alcohol, 0.3 g of palmitic acid, 4.0 g of spermaceti, 0.4 g of cholesterol, 0.4 g of cholesterol palmitate and 14.0 g of yolk lecithin. The glass bottle was shaken at 37° C. for 5 hours.

After five hours, the polymer was picked up from the artificial tear lipid solution and then, lipid components which adhered to the polymer were extracted by immersing the polymer in 1 ml of a mixed solution of ethanol and ether (ethanol:ether=3:1 (volume ratio)).

To 500 μl of the obtained lipid extracted solution was added 1 ml of concentrated sulfuric acid and then, 3 mg of vanillin and 2 ml of phosphoric acid were added thereto. Adhering lipid amount (mg/cm$^2$) of the polymer was quantitated.

When adhering lipid amount is more than 0.3 mg/cm$^2$, lipid easily adheres to the polymer. Thus, the polymer has poor lipid-stain resistance, and is not suitable for an ocular lens such as a contact lens or an intraocular lens.

Abbreviations in Tables 1 and 2 indicate the following compounds.

SiMa1: a macromonomer represented by the formula:

$$A-CH_2CH_2OCH_2CH_2CH_2-\underset{\underset{CH_3}{|}}{\overset{\overset{CH_3}{|}}{Si}}O-(\underset{\underset{CH_3}{|}}{\overset{\overset{CH_3}{|}}{Si}}O)_a-\underset{\underset{CH_3}{|}}{\overset{\overset{CH_3}{|}}{Si}}-CH_2CH_2CH_2OCH_2CH_2-A$$

wherein A is a group represented by the formula:

$$CH_2=\underset{\underset{H}{|}}{C}-COOCH_2CH_2-OCON\underset{H}{\overset{H}{|}}-\underset{H_3C\quad CH_3}{\bigcirc}\overset{CH_3}{-}CH_2-\underset{H}{\overset{H}{|}}NCOO-$$

in which a is an integer of 20 to 50;

whose number average molecular weight is 6,000; and having four urethane groups on average.

SiMa2: a macromonomer represented by the formula:

$$A'-CH_2CH_2OCH_2CH_2CH_2-\underset{\underset{CH_3}{|}}{\overset{\overset{CH_3}{|}}{Si}}O-(\underset{\underset{CH_3}{|}}{\overset{\overset{CH_2CF_3}{|}\;|\;CH_2}{Si}}O)_{a'}-(\underset{\underset{CH_3}{|}}{\overset{\overset{CH_3}{|}}{Si}}O)_{a''}-\underset{\underset{CH_3}{|}}{\overset{\overset{CH_3}{|}}{Si}}-CH_2CH_2CH_2OCH_2CH_2-A'$$

wherein A' is a group represented by the formula:

$$CH_2=\underset{\underset{H}{|}}{C}-COOCH_2CH_2-OCON\underset{H}{\overset{H}{|}}-\underset{H_3C\quad CH_3}{\bigcirc}\overset{CH_3}{-}CH_2-\underset{H}{\overset{H}{|}}NCOO-$$

in which a' is an integer of 10 to 20 and a" is an integer of 20 to 40;

whose number average molecular weight is 7,500; and having four urethane groups on average.

SiMa3: a macromonomer represented by the formula:

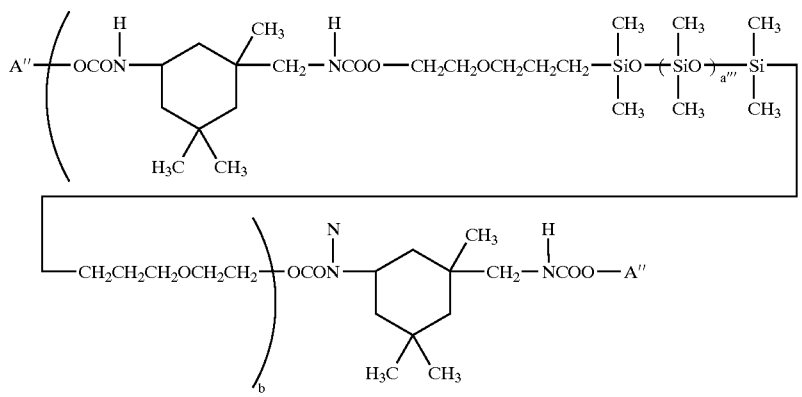

wherein A'' is a group represented by the formula:

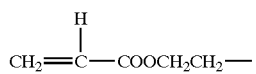

in which a''' is an integer of 5 to 25 and b is an integer of 1 to 5;
whose number average molecular weight is 9,000; and having eight urethane groups on average.
V1: vinyl acetate
V2: vinyl propionate
V3: vinyl pivalate SiMo1: tris(trimethylsiloxy)silylpropyl acrylate
SiMo2: tris(trimethylsiloxy)silylpropyl methacrylate
F1: 2-hydroxy-3-perfluorohexylpropyl acrylate
F2: 2-hydroxy-3-perfluorooctylpropyl acrylate
C1: ethylene glycol dimethacrylate
C2: diethylene glycol diallyl ether
2HEMA: 2-hydroxyethyl methacrylate
2HEA: 2-hydroxyethyl acrylate
DMAA: N,N-dimethylacrylamide
NVP: N-vinylpyrrolidone Number average molecular weights of the above SiMa1, SiMa2 and SiMa3 were converted to polystylene basis according to size exclusion chromatography.

TABLE 1

| | Monomer mixture (part) | | | | | | | | | | | |
|---|---|---|---|---|---|---|---|---|---|---|---|---|
| | (A) | | | (B) | | | (C) | | (D) | | (E) C1/C2 = 1/2 | |
| Ex. No. | SiMa1 | SiMa2 | SiMa3 | V1 | V2 | V3 | SiMo1 | SiMo2 | F1 | F2 | (weight ratio) | Saponification |
| 1 | 40 | — | — | 30 | — | — | 30 | — | — | — | 1 | not saponified |
| 2 | 40 | — | — | 30 | — | — | 30 | — | — | — | 1 | saponified |
| 3 | 20 | — | — | 40 | — | — | 40 | — | — | — | 1 | not saponified |
| 4 | 50 | — | — | 35 | — | — | 15 | — | — | — | 1 | saponified |
| 5 | — | 50 | — | 35 | — | — | 15 | — | — | — | 1 | saponified |
| 6 | — | — | 40 | 30 | — | — | 30 | — | — | — | 1 | saponified |
| 7 | 50 | — | — | 35 | — | — | — | 15 | — | — | 1 | saponified |
| 8 | 50 | — | — | — | 35 | — | 15 | — | — | — | 1 | saponified |
| 9 | 50 | — | — | — | — | 35 | 15 | — | — | — | 1 | saponified |
| 10 | 40 | — | — | 28 | — | — | 12 | — | 20 | — | 1 | saponified |
| 11 | 40 | — | — | 28 | — | — | 12 | — | — | 20 | 1 | saponified |

TABLE 2

| | Monomer mixture (part) | | | | | | | |
|---|---|---|---|---|---|---|---|---|
| | (A) | | (C) | (E) C1/C2 = 1/2 | Others | | | |
| Com. Ex. No. | SiMa1 | SiMa3 | SiMo1 | (weight ratio) | 2HEMA | 2HEA | DMAA | NVP | Saponification |
| 1 | 40 | — | 30 | 1 | 30 | — | — | — | not saponified |
| 2 | 40 | — | 30 | 1 | 30 | — | — | — | saponified |
| 3 | — | 40 | 30 | 1 | 30 | — | — | — | not saponified |
| 4 | 40 | — | 30 | 1 | — | 30 | — | — | not saponified |
| 5 | 40 | — | 30 | 1 | — | — | 30 | — | not saponified |
| 6 | 40 | — | 30 | 1 | — | — | — | 30 | not saponified |

TABLE 3

Properties of polymer (ocular lens material)

| Ex. No. | Oxygen permeability (DK value) | Shape recovery (Shape recovery coefficient (%)) | Surface wettability for water | Lipid-stain resistance (Adhering lipid amount (mg/cm²)) |
|---|---|---|---|---|
| 1  | 115 | 5  | ○ | 0.2≧ |
| 2  | 110 | 5  | ⊚ | 0.2≧ |
| 3  | 105 | 11 | ○ | 0.2≧ |
| 4  | 130 | 9  | ⊚ | 0.2≧ |
| 5  | 130 | 11 | ⊚ | 0.2≧ |
| 6  | 110 | 10 | ⊚ | 0.2≧ |
| 7  | 130 | 11 | ⊚ | 0.2≧ |
| 8  | 130 | 10 | ⊚ | 0.2≧ |
| 9  | 130 | 10 | ⊚ | 0.2≧ |
| 10 | 130 | 10 | ⊚ | 0.1≧ |
| 11 | 130 | 10 | ⊚ | 0.1≧ |

TABLE 4

| | Surface wettability for water of polymer (ocular lens material) (dynamic contact angle (°)) | Ultraviolet-ray irradiation |
|---|---|---|
| Ex. No. | | |
| 6 | 98 | not irradiated |
|   | 60 | irradiated |
| 10 | 95 | not irradiated |
|    | 60 | irradiated |
| Com. Ex. No. | | |
| 1 | 130 | not irradiated |
| 4 | 140 | not irradiated |

TABLE 5

Properties of polymer (ocular lens material)

| Com. Ex. No. | Oxygen permeability (DK value) | Shape recovery (Shape recovery coefficient (%)) | Surface wettability for water | Lipid stain resistance (Adhering lipid amount (mg/cm²)) |
|---|---|---|---|---|
| 1 | 110 | 25 | △ | 0.5 |
| 2 | 80  | 25 | ○ | 0.5 |
| 3 | 110 | 25 | △ | 0.5 |
| 4 | 110 | 9  | △ | 0.6 |
| 5 | 110 | 9  | △ | 0.6 |
| 6 | 110 | 6  | △ | 0.5 |

The results in Table 3 prove that a polymer which has high oxygen permeability, superior lipid-stain resistance, excellent surface wettability, and excellent shape recovery at the same time can be obtained when a siloxane macromonomer (A) and a vinyl ester of lower fatty acid (B) are used together as in Examples 1 to 11. The results also show that a polymer which has further improved surface wettability can be obtained when saponification is carried out as in Examples 2 and 4 to 11. It is also proved that a polymer which has particularly excellent lipid-stain resistance in addition to the above advantages can be obtained when a fluorine-containing monomer (D) is used as in Examples 10 and 11. The results in Table 4 indicate that when short wavelength ultraviolet ray is irradiated before saponification as in Examples 6 and 10, a polymer has smaller dynamic contact angle and more excellent surface wettability than those in Comparative Examples 1 and 4 and cases in Examples 6 and 10 where ultraviolet ray was not irradiated.

On the contrary, the results in Table 5 shows that when a hydrophilic monomer of 2-hydroxyethyl (meth)acrylate, N,N-dimethylacrylamide or N-vinylpyrrolidone is used instead of the vinyl ester of lower fatty acid (B) as in Comparative Examples 1 to 6, surface wettability is inferior as in Comparative Examples 1 and 3 to 6, shape recovery is poor as in Comparative Examples 1 to 3, and lipid-stain resistance is particularly low.

EXAMPLES 12 and 13

C.I. Reactive Blue 4 available from Mitsui BASF Dye Co., Ltd. was dissolved in 20 ml of distilled water in an amount of 0.0511 g to obtain a solution. To 20 ml of 2-propanol was added 1 ml of the above solution at 25° C. A siloxane-containing polymer obtained in the same manner as in Example 2 (Example 12), and a siloxane-containing polymer obtained in the same manner as in Example 10 without ultraviolet-ray irradiation before saponification (Example 13) were immersed in the mixture for 16 hours, respectively. Next, these polymers were immersed in the same methanol aqueous solution containing sodium hydroxide as used in Example 2 for 6 hours at 25° C., and then each polymer was taken out therefrom, transferred to distilled water, and taken out therefrom after 120 minutes.

All polymers assumed uniform and transparent blue color, and was equal to polymers obtained in Examples 2 or 10 in high oxygen permeability, and excellent lipid-stain resistance, surface wettability and shape recovery.

INDUSTRIAL APPLICABILITY

The ocular lens material of the present invention is excellent not only in lipid-stain resistance, wettability and oxygen permeability, but also in flexibility, particularly, shape recovery at the same time, and can be suitably used for ocular lenses such as soft contact lens and soft intraocular lens. According to the process of the present invention, the above ocular lens material is easily produced.

What is claimed is:

1. An ocular lens material comprising a siloxane-containing polymer obtained by polymerizing a monomer mixture containing (A) a siloxane macromonomer having at least two active unsaturated groups and a number average molecular weight of 2,000 to 100,000; (B) a vinyl ester of lower fatty acid; and (C) a silicon-containing monomer as essential components.

2. The ocular lens material of claim 1, wherein the weight ratio of the total of said siloxane macromonomer (A) and said silicon-containing monomer (C) to said vinyl ester of lower fatty acid (B), the total weight of (A) and (C)/the weight of (B), is 30/70 to 90/10.

3. The ocular lens material of claim 1, wherein the weight ratio of said siloxane macromonomer (a) to said silicon-containing monomer (c), the weight of (A)/the weight of (C), is at least 20/80.

4. The ocular lens material of claim 1, wherein said siloxane macromonomer (A) is a macromonomer represented by the formula (I-1):

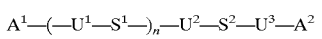  (I-1)

wherein each of $A^1$ and $A^2$ is independently an active unsaturated group, an active unsaturated group having an alkylene group having 1 to 20 carbon atoms or an active unsaturated group having an alkylene glycol group having 1 to 20 atoms; $U^1$ is a diurethane type group which contains urethane bonds formed with adjacent $A^1$ and adjacent $S^1$ on both sides or which contains urethane bonds with adjacent two $S^1$ on both sides; $U^2$ is a diurethane type group which contains urethane bonds formed with adjacent $A^1$ and adjacent $S^2$ on both sides or which contains urethane bonds with adjacent $S^1$ and adjacent $S^2$ on both sides; $U^3$ is a diurethane type group which contains urethane bonds formed with adjacent $S^2$ and adjacent $A^2$ on both sides; each of $S^1$ and $S^2$ is independently a group represented by the formula:

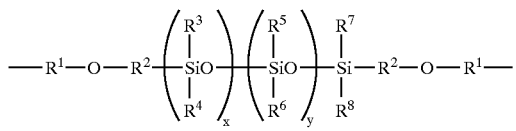

in which each of $R^1$ and $R^2$ is independently an alkylene group having 1 to 20 carbon atoms, each of $R^3$, $R^4$, $R^5$, $R^6$, $R^7$ and $R^8$ is independently a linear, branched or cyclic alkyl group having 1 to 20 carbon atoms which may be substituted with a fluorine atom, or a group represented by the formula:

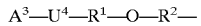

in which $A^3$ is an active unsaturated group, an active unsaturated group having an alkylene group having 1 to 20 carbon atoms or an active unsaturated group having an alkylene glycol group having 1 to 20 carbon atoms, $U^4$ is a urethane type group which contains urethane bonds formed with adjacent $A^3$ and adjacent $R^1$ on both sides, each of $R^1$ and $R^2$ is the same as the above, x is an integer of 1 to 1500, y is 0 or an integer of 1 to 1499, and x+y is an integer of 1 to 1500; and n is 0 or an integer of 1 to 10; or a macromonmer represented by the formula (I-2):

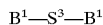 (I-2)

wherein $B^1$ is an active unsaturated group having urethane bond, and $S^3$ is a group represented by the formula:

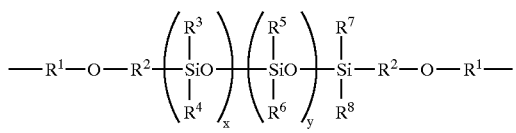

$R^1$ and $R^2$ is independently an alkylene group having 1 to 20 carbon atoms, each of $R^3$, $R^4$, $R^5$, $R^6$, $R^7$ and $R^8$ is independently a linear, branched or cyclic alkyl group having 1 to 20 carbon atoms which may be substituted with a fluorine atom, or a group represented by the formula:

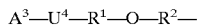

in which $A^3$ is an active unsaturated group, an active unsaturated group having an alkylene group having 1 to 20 carbon atoms or an active unsaturated group having an alkylene glycol group having 1 to 20 carbon atoms, $U^4$ is a urethane type group which contains urethane bonds formed with adjacent $A^3$ and adjacent $R^1$ on both sides, each of $R^1$ and $R^2$ is the same as the above, x is an integer of 1 to 1499, and x+y is an integer of 1 to 1500.

5. The ocular lens material of claim 1, wherein said vinyl ester of lower fatty acid (B) is a compound represented by the formula (II):

wherein R is hydrogen atom or an alkyl group having 1 to 15 carbon atoms which may be substituted with a halogen atom.

6. The ocular lens material of claim 1, wherein said vinyl ester of lower fatty acid (B) is vinyl acetate, vinyl propionate or vinyl pivalate.

7. The ocular lens material of claim 1, wherein said silicon-containing monomer (C) is a silicon-containing (meth)acrylate.

8. The ocular lens material of claim 1, wherein said silicon-containing monomer (C) is tris(trimethylsiloxy)silylpropyl acrylate.

9. An ocular lens material comprising a siloxane-containing polymer obtained by polymerizing a monomer mixture containing (A) a siloxane macromonomer having at least two active unsaturated groups and a number average molecular weight of 2,000 to 100,000; (B) a vinyl ester of lower fatty acid; and (D) a fluorine-containing monomer as essential components.

10. The ocular lens material of claim 9, wherein said fluorine-containing monomer (D) is a fluoroalkyl(meth)acrylate.

11. An ocular lens material comprising a siloxane-containing polymer obtained by polymerizing a monomer mixture containing (A) a siloxane macromonomer having at least two active unsaturated groups and a number average molecular weight of 2,000 to 100,000; (B) a vinyl ester of lower fatty acid; (C) a silicon-containing monomer; and (D) a fluorine-containing monomer as essential components, wherein the weight ratio of the total of said siloxane macromonomer (A), said vinyl ester of lower fatty acid (B) and said silicon-containing monomer (C) to said fluorine-containing monomer (D), the total weight (A), (B) and (C)/the weight of (D), is at least 20/80.

12. An ocular lens material comprising a polymer prepared by saponifying the siloxane-containing polymer of any one of claims 1, 9 or 11.

13. The process for producing an ocular lens material, characterized by preparing a siloxane-containing polymer by polymerization of a monomer mixture containing
    (A) a siloxane macromonomer having at least two active unsaturated groups and a number average molecular weight of 2,000 to 100,000; and
    (B) a vinyl ester of lower fatty acid as essential components; and then subjecting said siloxane-containing polymer to saponification.

14. The process of claim 13, wherein said saponification is carried out by alkali treatment.

15. The process of claim 14, wherein a methanol aqueous solution containing sodium hydroxide in a concentration of 0.01 to 1 mol/L is used for said alkali treatment as a treatment solution.

16. The process of claim 15, wherein the volume ratio of methanol to water in said methanol aqueous solution, methanol/water, is 30/70 to 90/10.

17. The process of claim 14, wherein after preparing said siloxane-containing polymer, a dye is dispersed in the siloxane-containing polymer and then, said dye is fixed to the siloxane-containing polymer during said saponification by said alkali treatment.

18. The process of claim 13, wherein after preparing said siloxane-containing polymer, a photo-irradiation is conducted and saponification is carried out subsequently.

19. The processing of claim 18, wherein said photo-irradiation is conducted by using ultraviolet ray whose wavelength is at most 380 nm.

20. The process of claim 18, wherein said photo-irradiation is conducted out by using ultraviolet ray whose wavelength is at most 300 nm.

21. The process of claim 18, wherein said photo-irradiation is conducted out for 0.1 to 600 minutes.

* * * * *